United States Patent [19]
Barnstead

[11] Patent Number: 6,036,928
[45] Date of Patent: Mar. 14, 2000

[54] PRESSURE STERILIZER

[76] Inventor: William A Barnstead, 19 Potter Pond, Lexington, Mass. 02173

[21] Appl. No.: 09/021,424

[22] Filed: Feb. 10, 1998

[51] Int. Cl.[7] .................................. A61L 2/00; A61L 2/16
[52] U.S. Cl. ........................... 422/295; 422/33; 422/106; 422/112; 137/587; 137/589
[58] Field of Search .................. 422/28, 33, 39, 422/292, 295, 105, 106, 112; 137/587, 589

[56] References Cited

U.S. PATENT DOCUMENTS

| | | | |
|---|---|---|---|
| 4,193,818 | 3/1980 | Young et al. .............................. | 422/33 |
| 4,239,730 | 12/1980 | Fahlvik et al. ............................ | 422/295 |
| 4,637,916 | 1/1987 | Hennebert et al. ....................... | 422/295 |
| 4,908,188 | 3/1990 | Jefferies, III et al. ................... | 422/295 |
| 5,132,084 | 7/1992 | Harrell et al. ............................ | 422/295 |
| 5,145,641 | 9/1992 | Shelley .................................... | 422/295 |

Primary Examiner—Krisanne Thornton
Assistant Examiner—Fabriborz Moazzam

[57] ABSTRACT

A sterilizing machine facilitates the introduction of a bath liquid into empty crevasses in the article to be sterilized by evacuating a chamber holding the article to be sterilized prior to covering the article with a bath of liquid. The sterilizer equipment also applies a high pressure to the article to enhance killing of organisms contained therein.

10 Claims, 1 Drawing Sheet

PRESSURE STERILIZER

BRIEF SUMMARY OF THE INVENTION

This invention relates to sterilizing machines for decontaminating articles of dangerous biological material, and especially to those using high pressures to do so.

Certain articles such as endoscopes present difficulties in sterilization because they cannot be exposed to the high temperatures used in conventional steam sterilizing and also because as a result of their construction they have small crevices which are not easily penetrated when the article is placed in a bath of biocide fluid. A sterilizing machine according to the present invention facilitates the introduction of a bath liquid into empty crevices in the article by evacuating a chamber holding an article to be sterilized prior to covering the article with a bath of liquid. The sterilizer equipment also applies a high pressure to the article to enhance killing of organisms contained therein.

DETAILED DESCRIPTION

Figure 1:
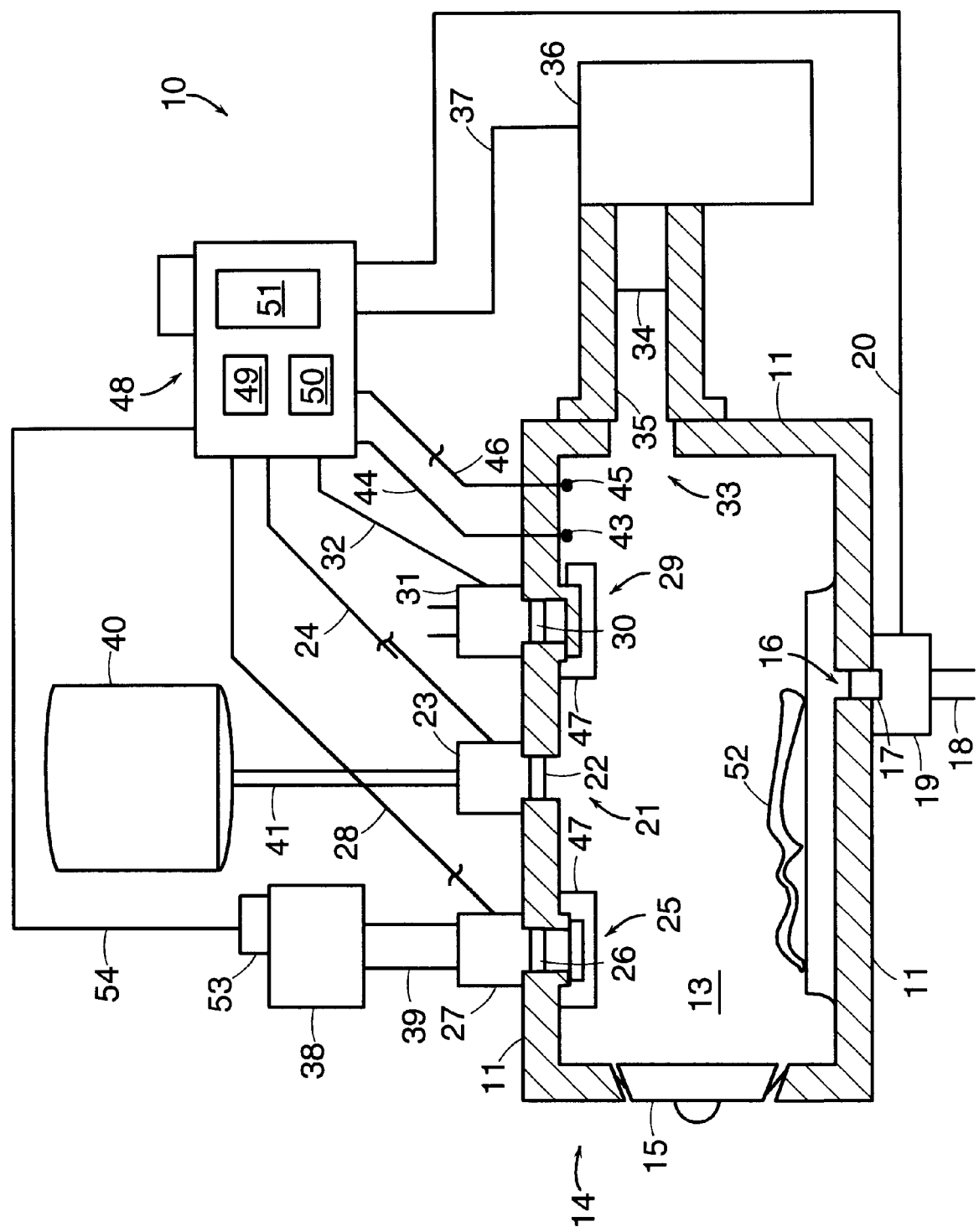
FIG. 1 shows schematically a sterilizing machine according to the invention.

The invention may be described with reference to the FIGURE. Machine 10 for sterilizing contaminated objects such as endoscope 52, comprises wall 11 enclosing an interior space 13. Access port 14 passes through wall 11. Access door 15 opens to give access to interior space 13 and closes to seal access port 14.

Drain port 16 passes through wall 11. Drain valve 17 opens to pass drainage through drain port 16 to drain 18 and closes to seal drain port 16. Drain valve driver 19 controls operation of drain valve 17 in response to control signals it receives on drain valve command line 20.

Inlet port 21 passes through wall 11. Inlet valve 22 opens to pass material through inlet port 21 and closes to seal inlet port 21. Inlet valve driver 23 controls operation of inlet valve 22 in response to control signals it receives on command line 24.

Exhaust port 25 passes through wall 11. Exhaust valve 26 opens to pass material through exhaust port 25 and closes to seal exhaust port 25. Exhaust valve driver 27 controls operation of exhaust valve 26 in response to control signals it receives on command line 28.

Vent port 29 passes through wall 11. Vent valve 30 opens to pass material through vent port 29 and closes to seal vent port 29. Vent valve driver 31 controls operation of vent valve 30 in response to control signals it receives on command line 32.

Pressurizing port 33 passes through wall 11, and is fitted with a pressure generator 34 such as piston 34 which moves in cylinder 35 to drive material into interior space 13 at high pressure. Pressure generator driver 36 is connected to pressure generator 34 and controls the motion thereof in accordance with signals it receives on command line 37.

Vacuum pump 38 is connected to exhaust port 25 through conduit 39 and exhaust valve 26. Vacuum pump controller 53 controls the operation of vacuum pump 38 in accordance with signals received on control line 54. Bath liquid supply tank 40 is connected to inlet port 21 through pipe 41 and inlet valve 22. Pressure sensor 43 is mounted within interior space 13 and emits a signal indicating the pressure within interior space 13 on signal line 44. Liquid level sensor 45 is mounted within interior space 13 and emits a signal indicating the liquid level in interior space 13 on signal line 46. Filters 47 are fitted over exhaust port 25 and vent port 29. These filters have an effective mesh size to prevent passage of any viable organisms to pass into the ports.

Operations controller 48, which includes processor 49, clock 50, and signal storage 51, is connected to control operation of the sterilizer in accordance with signals stored in signal storage 51. Controller 48 is connected to receive signals on signal lines 44 and 46 and to emit control signals on command lines 20, 24, 28, 32, 37, and 54.

As an example of the use of the sterilizing machine according to the invention, an article to be sterilized, such as a used endoscope, is placed inside the sterilizer cavity and the door closed. Then the operations controller in accordance with operating signals stored therein and sensor signals it receives from time to time, initiates the following sequence. Piston 34 is withdrawn; the drain valve is closed; the exhaust valve is opened; the inlet valve is closed; the vent valve is closed. The vacuum pump is then put in operation. As the interior space is evacuated and the pressure therein falls, aqueous material in crevices of the article will be vaporized and flow out of the crevices, and will be then drawn out of the interior space through the filter and the exhaust port. Any organisms, however, will be trapped in the filter and not enter the environment. The controller, after an interval determined by reference to its program and to signals from the pressure sensor, will close the exhaust valve and open the inlet valve. This will admit bath liquid, which may have germicidal activity, to cover the article and begin to fill the interior space. As the bath liquid flows into the interior space, the pressure will rise and bath liquid will be forced into the previously evacuated crevices of the article. When the pressure in the interior space rises to atmospheric (as sensed by the pressure sensor), the controller will open the vent valve to permit expulsion of all residual gases and permit the interior space to completely fill with bath liquid. When the level sensor senses that the bath liquid has completely filled the interior space, the controller will close the inlet valve and the vent valve and start the pressure generator. The pressure generator may be operated to generate, for an interval determined by the controller with reference to its stored program, a moderate pressure, which may be about 300 psi, in the interior space to activate and make more susceptible to killing spores and the like. After such interval, the controller operates the pressure generator to produce and maintain a higher and lethal pressure, which may be 15000 psi. After an interval again determined by the controller with reference to its stored program, the controller terminates the action of the pressure generator and opens the drain valve and the vent valve. This will result in the bath liquid draining out of the interior space through the drain port. After the bath liquid has drained, the controller closes the drain valve, closes the vent valve, and activates the vacuum pump for an interval. This results in drying residual liquid on the article. After the drying is complete, the controller turns off the vacuum pump and opens the vent valve to bring the pressure within the interior space to atmospheric. The door can then be opened and the now sterilized article removed.

It will be recognized that the sterilizing machine of the invention can be used with a variety of bath liquids and operating cycles depending on circumstances.

What is claimed is:

1. A machine for sterilizing contaminated objects comprising an enclosure with a wall enclosing an interior space, an access port passing through said wall and an access door that opens to give access to said interior space through said access port and closes to seal said access port, a first port passing through said wall, said first port including a first valve controlling flow through said first port, a drain being connected to said first port, a second port, distinct from said first port, passing through said wall, said second port including a second valve controlling flow through said second port, a bath liquid supply being connected to said second port, a third port, distinct from said first and second ports, passing through said wall, said third port including a third valve controlling flow through said third port, a vacuum pump being connected to said third port, a fourth port, distinct from said first, second, and third ports, passing through said wall, said fourth port being fitted with a pressure generator for driving material into said interior space at high pressure, a pressure sensor arranged to emit a signal indicating the pressure in said interior space, and a liquid sensor arranged to emit a signal indicating whether the interior space is filled with liquid.

2. A sterilizing machine as claimed in claim 1, further comprising a first valve driver connected to said first valve and operating said first valve in accordance with control signals which it receives, a second valve driver connected to said second valve and operating said second valve in accordance with control signals which it receives, a third valve driver connected to said third valve and operating said third valve in accordance with control signals which it receives, a pressure generator driver connected to said pressure generator and operating said pressure generator in accordance with signals which it receives, a vacuum pump controller operating said vacuum pump in accordance with signals which it receives, and an operations controller connected to receive signals from said pressure sensor and from said liquid sensor and to send control signals to said first valve driver, to said second valve driver, to said third valve driver, to said vacuum pump controller, and to said pressure generator driver.

3. A sterilizing machine as claimed in claim 1, including a fifth port passing through said wall, said fifth port including a fifth valve controlling flow through said fifth port, said fifth port opening to ambient.

4. A sterilizing machine as claimed in claim 1, including a filter attached across said third port, said filter being of a mesh to catch spores.

5. A machine for sterilizing contaminated objects comprising an enclosure with a wall enclosing an interior space, an access port passing through said wall and an access door that opens to give access to said interior space through said access port and closes to seal said access port, a first port passing through said wall, said first port including a first valve controlling flow through said first port, a drain being connected to said first port, a second port, distinct from said first port, passing through said wall, said second port including a second valve controlling flow through said second port, a bath liquid supply being connected to said second port, a third port, distinct from said first and second ports, passing through said wall, said third port including a third valve controlling flow through said third port, a vacuum pump being connected to said third port, a liquid level sensor arranged to emit a signal indicating the level of liquid in said interior space.

6. A sterilizing machine as claimed in claim 5, further comprising a first valve driver connected to said first valve and operating said first valve in accordance with control signals which it receives, a second valve driver connected to said second valve and operating said second valve in accordance with control signals which it receives, a third valve driver connected to said third valve and operating said third valve in accordance with control signals which it receives, a vacuum pump controller operating said vacuum pump in accordance with signals which it receives, and an operations controller connected to receive signals from said liquid level sensor and to send control signals to said first valve driver, to said second valve driver, to said third valve driver, and to said vacuum pump controller.

7. A machine for sterilizing contaminated objects comprising an enclosure with a wall enclosing an interior space, an access port passing through said wall and an access door that opens to give access to said interior space through said access port and closes to seal said access port, a first port passing through said wall, said first port including a first valve controlling flow through said first port, a drain being connected to said first port, a second port, distinct from said first port, passing through said wall, said second port including a second valve controlling flow through said second port, a bath liquid supply being connected to said second port, a third port, distinct from said first and second ports, passing through said wall, said third port being fitted with a pressure generator for driving material into said interior space at high pressure, a fourth port, distinct from said first, second, and third ports, passing through said wall, said fourth port including a third valve controlling flow through said fourth port, said fourth port being connected to ambient, a pressure sensor arranged to emit a signal indicating the pressure in said interior space, and a liquid sensor arranged to emit a signal indicating whether the interior space is filled with liquid.

8. A sterilizing machine as claimed in claim 7, further comprising a first valve driver connected to said first valve and operating said first valve in accordance with control signals which it receives, a second valve driver connected to said second valve and operating said second valve in accordance with control signals which it receives, a third valve driver connected to said third valve and operating said third valve in accordance with control signals which it receives, a pressure generator driver connected to said pressure generator and operating said pressure generator in accordance with signals which it receives, and an operations controller connected to receive signals from said pressure sensor and from said liquid level sensor and to send control signals to said first valve driver, to said second valve driver, to said third valve driver, and to said pressure generator driver.

9. A machine for sterilizing contaminated objects comprising an enclosure with a wall enclosing an interior space, an access port passing through said wall and an access door that opens to give access to said interior space through said access port and closes to seal said access port, a first port passing through said wall at the bottom of said enclosure, said first port including a first valve controlling flow through said first port, a second port passing through said wall at the top of said enclosure, said second port including a second valve controlling flow through said second port, a pressure generator connected to said wall, a bath liquid supply connected to supply the interior space with bath liquid through a port distinct from said second port, said first port being connected to discharge liquid from said interior space to drain, said second port being connected to exhaust gas from said interior space to ambient, said wall, said access port, said first port, said first valve, said second port and said second valve being constructed so as to sustain a pressure higher than 300 psi within said interior space, said pressure generator being constructed to be able to drive material into said interior space at pressure in excess of 300 psi.

10. A machine as claimed in claim 9, wherein said wall, said access port, said first port, said first valve, said second port and said second valve are constructed so as to sustain a pressure of 15000 psi within said interior space, and said pressure generator is constructed to be able to drive material into said interior space at pressure of 15000 psi.

* * * * *